United States Patent
Fruehwirth et al.

(10) Patent No.: US 8,269,845 B2
(45) Date of Patent: Sep. 18, 2012

(54) METHOD FOR OPTICALLY DETECTING MOVING OBJECTS

(75) Inventors: Josef Fruehwirth, Graz (AT); Axel Kulcke, Weichselbaum (AT)

(73) Assignee: EVK DI Kerschhaggl GmbH, Raaba (AT)

( * ) Notice: Subject to any disclaimer, the term of this patent is extended or adjusted under 35 U.S.C. 154(b) by 129 days.

(21) Appl. No.: 12/943,881

(22) Filed: Nov. 10, 2010

(65) Prior Publication Data

US 2011/0050968 A1    Mar. 3, 2011

Related U.S. Application Data

(63) Continuation of application No. PCT/AT2009/000193, filed on May 11, 2009.

(30) Foreign Application Priority Data

May 13, 2008 (AT) .................. A 760/2008

(51) Int. Cl.
*H04N 9/04* (2006.01)
*H04N 1/46* (2006.01)
*G01N 21/00* (2006.01)

(52) U.S. Cl. ............... 348/210.99; 358/506; 356/73

(58) Field of Classification Search ......... 348/209.99, 348/210.99, 269, 294, 308; 358/505, 506, 358/509, 512; 356/73, 320, 456; 396/155
See application file for complete search history.

(56) References Cited

U.S. PATENT DOCUMENTS

| | | | |
|---|---|---|---|
| 5,432,607 A * | 7/1995 | Taubenblatt | 356/364 |
| 6,137,074 A | 10/2000 | Doak | |
| 7,019,822 B1 | 3/2006 | Doak et al. | |
| 2006/0153558 A1* | 7/2006 | Tan et al. | 396/155 |
| 2008/0043224 A1* | 2/2008 | Castonguay et al. | 356/73 |
| 2008/0212078 A1* | 9/2008 | Teich et al. | 356/73 |

FOREIGN PATENT DOCUMENTS

| | | |
|---|---|---|
| AT | 004 889 U1 | 12/2001 |
| AT | 410 847 B | 8/2003 |
| AT | 503 036 A4 | 7/2007 |

(Continued)

OTHER PUBLICATIONS

The International Search Report having a date of mailing of Oct. 30, 2009 for PCT/AT2009/000193, filed May 11, 2009 (in 3 pages).

(Continued)

*Primary Examiner* — Trung Diep

(74) *Attorney, Agent, or Firm* — Knobbe Martens Olson & Bear LLP

(57) ABSTRACT

A process for the optical detection of objects moved at a conveying speed. The process comprises illuminating the object in a temporally consecutive manner with a sequence of at least two light pulses of different colors and taking images of the object during each light pulse with a monochromatic optical area sensor comprising many sensor lines. The process comprises reading out and temporarily storing at least as many lines of each image as there are different colors of the light pulses. The read-out lines have a line pitch relative to each other. Sequentially combining lines from images taken under illumination by different colors to form color lines, with the lines combined with each other having the aforesaid line pitch or a multiple thereof relative to each other when they are being read out, and assembling the color lines into an overall color picture.

11 Claims, 4 Drawing Sheets

FOREIGN PATENT DOCUMENTS

| | | |
|---|---|---|
| DE | 195 11 534 A1 | 10/1996 |
| DE | 100 63 293 A1 | 7/2002 |
| EP | 1 030 173 A1 | 8/2000 |
| EP | 1 742 041 A1 | 1/2007 |
| JP | 11277000 A | 12/1999 |
| JP | 2002205019 A | 7/2002 |
| WO | WO 2007/095946 A1 | 8/2007 |

OTHER PUBLICATIONS

The PCT Written Opinion of the International Searching Authority dated Oct. 30, 2009 for PCT/AT2009/000193, filed May 11, 2009 (in 7 pages).

English Translation of PCT Written Opinion of the International Searching Authority dated Oct. 30, 2009 for PCT/AT2009/000193, filed on May 11, 2009 in 6 pages.

* cited by examiner

METHOD FOR OPTICALLY DETECTING MOVING OBJECTS

CROSS-REFERENCE TO RELATED APPLICATIONS

This application is a continuation of International Application No. PCT/AT2009/000193, filed May 11, 2009, which claims the benefit of Austrian Patent Application No. A 760/2008, filed May 13, 2008, both of which are hereby incorporated by reference.

BACKGROUND OF THE INVENTION

1. Field of the Invention

The invention relates to a process for the optical detection of objects moved at a conveying speed.

2. Description of the Related Art

The detection and subsequent sorting of bulk materials with color cameras is an established method. A common embodiment variant is described, for example, in Patent AT 410847. This technology is used in particular in the field of recycling. In doing so, a transmitted light detection and a sorting are predominant in which glass and transparent synthetic products are processed by radiating light through them, collecting the light passing through by means of the color camera and analyzing it. In this technology, however, labels or the like on the transparent glass and plastic parts constitute considerable obstacles so that costly mechanical methods, see, e.g., AT 503036 B1, are even employed for their removal in a pre-stage of the process. However, for improving the yield, it is absolutely desirable that transparent objects are identified although non-transparent foreign matters, such as labels, stick to them.

Furthermore, fluorescent tube systems or LED-based lighting systems (disclosed, e.g., in utility model AT 004889U1) are also used nowadays. The advances in optical technology provide color cameras with higher and higher line scanning rates which, however, in turn require shorter and shorter illumination times and thus higher luminances for illuminating the objects to be detected. The high luminances required for systems with line scanning rates of 4-20 kHz, which are already prior art or will be available in the near future, can no longer be achieved with fluorescent tubes or thermal illuminants. Therefore, it has already been suggested that systems be equipped with light emitting diodes (LEDs) as illuminants in order to increase the luminance. Beam focussing optical systems in combination with a generation of white light by means of blue LEDs with yellow fluorescent dyes (so-called white light LEDs) have become established as a standard in this field. However, due to the inefficient color conversion, this type of illumination requires an active cooling, which is accomplished, for example, by water coolings in a costly manner.

Color cameras with color filters on the optically sensitive elements (pixels) or 3-chip cameras are today used as standard technology in connection with white light illumination, wherein one chip each is sensitive to one of the three primary colors red, green, blue. Furthermore, the demand made on the resolution and hence the number of pixels is getting larger and larger. Today, more than 1000 color triples are already standard, and developments are aimed at raising the limit by one order of magnitude. This requires a further reduction in pixel size, which, in turn, further increases the demands made on the luminance of the lighting equipments, and also a decrease in the quality of the color filters, which are questionable, anyway. In 3-chip cameras, the required optical splitting of the optical paths for separating the color components and the adjustment of the sensors relative to each other are to be assessed as critical.

Thus, the need for an improved process for the optical detection of moving objects still exists which provides a high quality of identification at high conveying speeds of the objects to be detected, but at the same time is able to get by with lighting equipments of comparatively low luminances.

SUMMARY OF THE INVENTION

In some embodiments, a process can optically detect an object moved at a conveying speed. The process comprises illuminating the object in a consecutive manner with a sequence of at least two light pulses having different colors. The process comprises taking images of the object during each light pulse with a monochromatic optical area sensor, the sensor including a plurality of sensor lines. The process comprises reading out and storing at least one line per image for each of the colored light pulses. The read-out lines can have a line pitch, and at least one line pitch can correspond to the movement of the projection of the object on the sensor between consecutive light pulses and to the movement of the object between light pulses when the object is moved at the conveying speed. The process comprises sequentially combining lines from images taken under illumination with different colors to form color lines, and each of the combined lines can be separated from each other by the at least one line pitch at the time of line read out. The process comprises assembling the color lines into a complete color picture.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION OF THE PREFERRED EMBODIMENT

Figure 1:
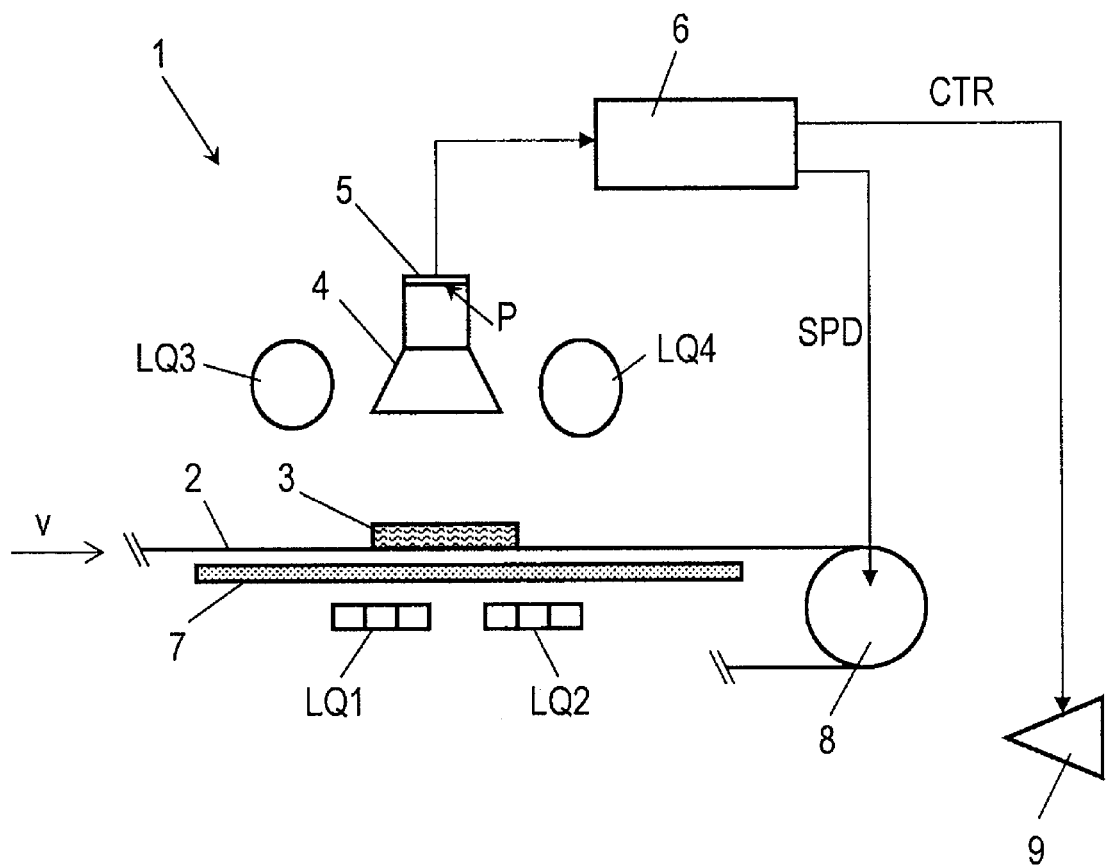
FIG. 1 shows a schematic block diagram of a system according to the invention for the optical detection and subsequent sorting of objects moved at a conveying speed.

The present invention is based on the problem of providing a process for the optical detection of moving objects which overcomes the disadvantages of the prior art as illustrated above.

This problem is solved by a process for the optical detection of moving objects having the characterizing features of claim 1. Further advantages and features of the present invention become apparent from the subclaims and the subsequent specification.

According to the invention, a pure monochrome sensor without upstream optical filters is used and the object is exposed sequentially to a sequence of light pulses in pre-defined colors, e.g., red, green, blue. With every light pulse, an image of the object is taken with the monochromatic area sensor and temporarily stored. Only a few lines of each image are required for the evaluation, which minimizes the amount of data to be processed. This design according to the invention has the advantage that each color component gets directly to the sensor and generates the signals there. By contrast, when, as is known, a color filter camera with RGB-exposure is used, the blue and green pixels have no significance for the red light and the red signal component, since the light is absorbed in the color filter, anyway. The same applies to the other colors. If, in addition, the non-ideal technical implementations of the color filters with very small pixel sizes, which allow only about 50% of the light quanta to reach the sensor, are taken as a basis, the result of the invention is a required luminance of the illumination which typically has been reduced to one sixth. A further clear reduction in the requirement for light is achieved by using the two-dimensional sensor in that, with every light pulse, several lines are exposed and, subsequently, the lines and the color information are assembled sequentially.

A high quality of object detection and a high processing speed are achieved if fast-switching, narrowband to monochromatic light sources, preferably light emitting diodes or lasers, are used for the illumination. For the sequential generation of RGB-images, the use of red (e.g., 630 nm), green (e.g., 530 nm) and blue (e.g., 460 nm) LEDs is advantageous. These LED types are typically realized in AlGaInP and InGaN technology and require no color conversion layer. Therein, the 3 LED types are preferably integrated together in a light source module in a tight arrangement. In this manner, a high luminance is achieved with a small heat production. A further advantage is that said light corresponds to the color filter curves of common filter cameras and, thus, a high-quality color representation is ensured. The luminous power which is clearly higher than in the prior art allows to work without optical focussing, which results in an illumination of the object which, to begin with, is more diffuse.

The present invention is suitable both for an incident light and a transmitted light illumination. When utilizing transmitted light illumination, primarily transparent or semitransparent objects are detected. When utilizing incident light illumination, also (partly) non-transparent objects can be detected.

Furthermore, the invention is suitable both for direct lighting systems (bright field), which today are used mostly in glass sorting, and for indirect lighting systems (dark field), in which the object is not irradiated directly, but is illuminated diffusely only via reflective surfaces and diffusers. When it is applied in the field of glass sorting, one is faced with broken objects which, on the one hand, have sharp breaking edges in all orientations and, on the other hand, often do not have plane-parallel surfaces, but lenticular surfaces. Furthermore, pigments are present in the objects, and the surfaces are frequently covered with labels or contaminations. In a bright-field illumination, these characteristics as described create major problems for the evaluation of the objects so that at least one proportionate dark-field illumination might be favourable.

In one embodiment of the invention, the sequence of light pulses is adjusted such that the projection of the object between two light pulses moves along by precisely one line pitch existing between the lines to be read out, wherein lines from the images taken in different colors under a consecutive illumination are combined sequentially to form the color lines, with the combined lines having the aforesaid line pitch relative to each other.

In an advanced development of this embodiment, a number of lines is read out from the images generated with every light pulse and is temporarily stored, which number is a multiple of, at least, however, twice the number of different colors of the light pulses. If, for example, sequences of light pulses are emitted in the colors red, green, blue, at least six lines per image have to be read out. Then, those lines are sequentially added up which have been recorded under illumination with the same color and which depict the same linear range of the object. Interlines of each illumination color which have been calculated in this way and which, in each case, depict the same linear range of the object are subsequently assembled into color lines and these are, in turn, assembled into an overall picture of the object. By adding up the corresponding lines of equal colors, a signal amplification takes place which reduces the required luminous intensity of the illumination to a respective fraction and thus contributes to a reduced power consumption and an increased lifetime of the light sources.

In an alternative embodiment of the process according to the invention, the sequence of the light pulses is adjusted such that the projection of the object between two light pulses moves along by an integral multiple of, at least twice, the line pitch between the lines to be read out, wherein lines from the images taken under illumination in different colors are combined sequentially to form the color lines, with the combined lines having the aforesaid multiple of the line pitch relative to each other. Said embodiment provides the advantage over the above-illustrated embodiments that the frequency of the light pulses can be reduced to a fraction, more precisely, the frequency is inversely proportional to the multiple of the line pitches by which the object moves along between two light pulses. In order to nevertheless achieve the same line resolution as with the above embodiments, the number of lines to be read out has to be increased to a respective multiple.

A further essential advantage of the invention is that it is possible to determine and to readjust the conveying speed of the objects from the signals of the combined color lines or to adjust the behaviour of reading out lines. It has namely been shown that, in the detection according to the invention, a clear sequence of illumination colors is apparent in the representation of the objects on the edges thereof, which sequence, however, yields in combination with each other a grey scale value (without a resulting color portion). If, however, a resulting color portion arises, this allows the conclusion that the timing of the sequence of light pulses and the line pitch of the read-out lines, respectively, do not correspond precisely to the conveying speed of the objects. Furthermore, it is possible to discern from the resulting color whether the conveying speed is too low or too high and also by how much the conveying speed deviates from the desired value, which is precisely known from the preadjustment of the sequence of light pulses and of the line pitch. The knowledge about the deviation of the actual speed from the desired conveying speed is in principle a speed measurement of the object, which is very important for sorting plants, since it is possible to determine therefrom when the object will reach a sorting device arranged downstream of the detection device more precisely than it would be possible if merely the desired speed was taken as a basis. Furthermore, it must be considered that the speed in an object flow rate is absolutely not uniform (e.g., caused by varying frictions on a conveyor chute) and that, by being aware of the actual speed of individual objects, a substantially higher accuracy in sorting the objects is achieved. Furthermore, the measurement according to the invention of the actual conveying speed can be used for readjusting an object transport device to the desired conveying speed. A further application of the measurement according to the invention of the actual conveying speed of the objects consists in readjusting the preset line pitch of the read-out lines until a color portion is no longer visible in the overall picture of the object on the object's edges. Complex calibration and recalibration operations can be omitted due to this self-adjusting system.

The invention is now illustrated in further detail on the basis of a non-limiting exemplary embodiment, with reference to the drawings.

With reference to FIG. 1, an exemplary embodiment of a system 1 according to the invention for the optical detection of objects 3 moved at a conveying speed v is now illustrated in further detail. The system 1 comprises a transport device 2 in the form of a conveyor belt. As an alternative, for example, a conveyor chute might also be considered. The transport device 2 is driven by a drive roll 8 at a predetermined conveying speed v. On the transport device 2, an object 3 is conveyed which is to be detected by the system 1. The object is, for example, a transparent piece of glass or plastic which is to be sorted out from a material stream. Alternatively, however, the object 3 may also be a non-transparent part, e.g., a stone, which is to be sorted out from a material stream of glass. However, the applications for the system 1 according to the invention are not limited to the examples illustrated here. A camera 4 comprising a monochromatic (black/white) area sensor 5 for detecting projections P of the object 3 which have been radiated onto the surface of the area sensor 5 by the optical system of the camera 4 is located above the transport device 2. Suitably, the optical axis of the camera 4 is directed at the transport device 2 at right angle. In this connection, it should be mentioned that, in practice, a plurality of objects 3 are of course detected simultaneously and that, for a more precise differentiation, usually a plurality of cameras 4 are arranged transversely to the conveying direction of the transport device 2. However, for the purpose of illustrating the invention, only one object 3 and one camera 4 are referred to.

For illuminating the object 3, a plurality of light sources LQ1, LQ2, LQ3, LQ4 are provided. In order to show that the system 1 according to the invention is suitable both for transmitted light processes and for incident light processes, two light sources LQ1, LQ2 are arranged beneath the transport device 2, which is exemplary of the transmitted light process, and two light sources LQ3, LQ4 are arranged above the transport device 2, i.e., on the same side of the transport device 2 as the camera 4, which is exemplary of the incident light process. For the transmitted light process, it is of course necessary that the transport device 2 is transparent, e.g., comprises a conveyor belt made of a transparent synthetic material. A diffuser plate 7 serves for homogenizing the light supplied by the light sources LQ1, LQ2. All light sources LQ1-LQ4 exhibit fast-switching, narrowband to monochromatic illuminants and are designed, for example, as luminaire profiles arranged across the transport device 2. In the present exemplary embodiment, the light sources LQ1, LQ2 are designed as modules including several rows of LEDs in different colors, e.g., red LEDs with a wavelength of 630 nm, green LEDs with a wavelength of 530 nm and blue LEDs with a wavelength of 460 nm. In operation, only LEDs of the same color are switched on simultaneously, as will be described in detail below. Light source LQ3 can be designed, for example, as an ultraviolet lamp, and light source LQ4 can be designed as an infrared lamp.

The monochromatic optical area sensor 5 is designed as an array of sensor dots arranged in lines and columns (typically 1024×1024 pixels), wherein the luminance signals of the pixels can be read out line by line. In a preferred embodiment, the area sensor 5 is designed as a CMOS sensor. The luminance values of the area sensor 5 are read out line by line by a computer 6, are temporarily stored and evaluated according to the detection process according to the invention described below. The result of the evaluation is, on the one hand, a control output signal CTR, which activates at least a subsequent sorting device 8, and, on the other hand, a speed control signal SPD, which readjusts the velocity of the drive roll 8.

Figure 2:
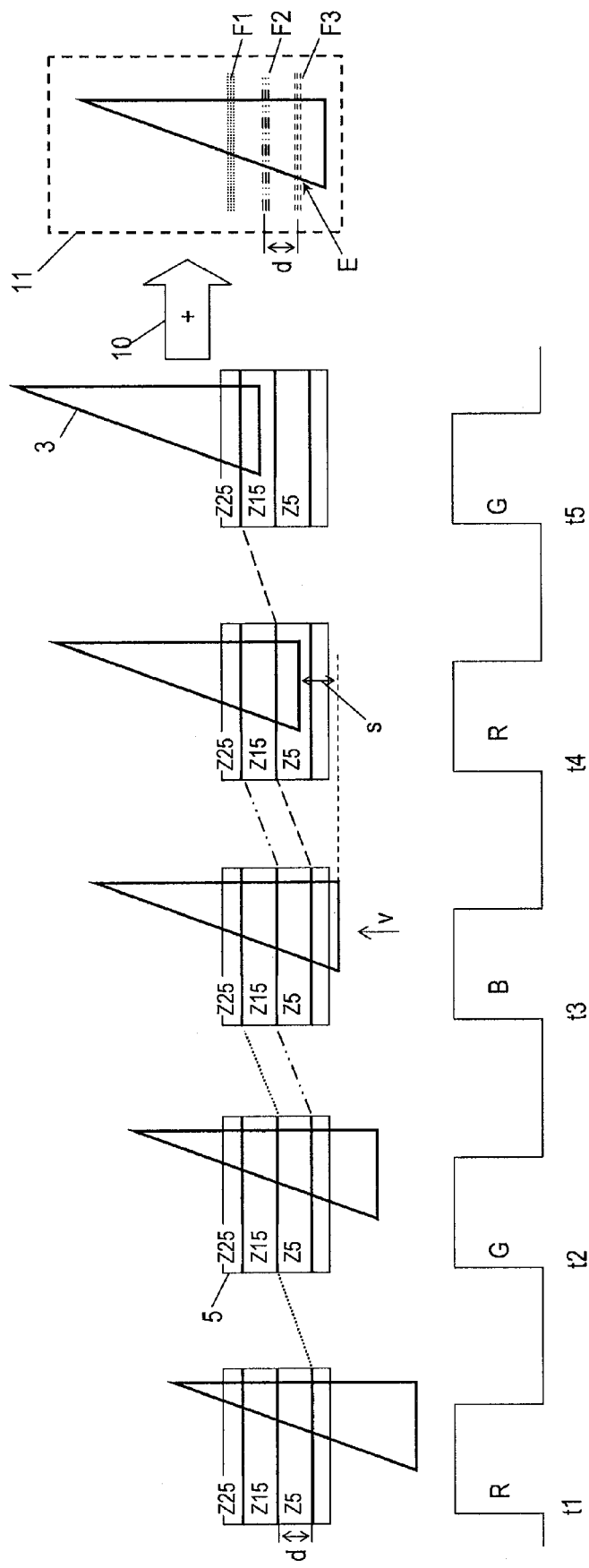
FIG. 2 shows a first path-time characteristic of a temporal sequence of light pulses and image recordings by an optical area sensor and the corresponding route of the object in the conveying direction.

Next, the process according to the invention for the optical detection of objects 3, which process is executed in the optical detection system 1, is explained with reference to FIG. 2. FIG. 2 shows top views of the monochromatic area sensor 5 at different instants t1, t2, t3, t4, t5, wherein, for the purpose of simplifying the illustration, it is assumed that it comprises merely 30 sensor lines. Furthermore, FIG. 2 shows the progression of path of the object 3 in the conveying direction (or, to be exact, its projection onto the sensor surface) at instants t1, t2, t3, t4, t5. For the subsequent explanation, the simplifying assumption suffices that the outlines of the real object 3 and of its projection on the surface of the sensor 5 generated by the optical system of the camera 4 coincide in the drawing.

According to the invention, the object 3 is illuminated with a sequence of light pulses comprising one respective light pulse at instants t1, t2, t3, t4, t5, wherein consecutive light pulses have different colors. It can be assumed that, at instant t1, a red light pulse R is emitted onto the object 3 by the red LEDs of light sources LQ1, LQ2, LQ3 and/or LQ4 of the system illustrated in FIG. 1 in the incident light and/or transmitted light process. At instant t2, a green light pulse G is emitted onto the object 3 by the green LEDs of light sources LQ1, LQ2, LQ3 and/or LQ4, and at instant t3, a blue light pulse B is emitted onto the object 3 by the blue LEDs of light sources LQ1, LQ2, LQ3 and/or LQ4. The light pulses R, G, B are illustrated as square wave signals in FIG. 2. The sequence of the light pulses R, G, B is arbitrary, but is repeated periodically with a constant pattern. The periodic repeat of the light pulses is illustrated for instants t4 and t5.

At instants t1, t2, t3, t4, t5 of a light pulse, an image of the object taken by the area sensor 5. However, not all lines are read out from this respective image by the computer 6, but only particular ones, namely at least so many lines of each image as there are different colors of the light pulses, i.e., three lines in this example. Furthermore, the read-out lines must have a line pitch d relative to each other which corresponds to the distance by which the projection of the object 3 onto the area sensor 5 moves along between consecutive light pulses. This line pitch d is proportional to the distance s for which the real object 3 moves along between consecutive light pulses at the conveying speed v in the conveying direction. It is to be assumed in accordance with practical implementations of the invention that the time intervals between the instants t1, t2, t3, t4, t5 at which the light pulses R, G, B, R, G occur are identical and that the conveying speed v is uniform or variable so slowly, respectively, that a uniform conveying speed between the individual light pulses can be assumed. Under these conditions it follows that the line pitch is constant and, in the present exemplary embodiment, has been assumed to comprise 10 lines. Thus, for example, the lines Z5, Z15 and Z25 are read out from each image and are temporarily stored.

Subsequently, the temporarily stored lines from the images taken under illumination in different colors with the consecutive light pulses R, G, B, R, G at instants t1, t2, t3, t4 and t5 are combined with each other in the computer 6 by means of an addition algorithm 10 to form color lines F1, F2, F3, in consideration of the fact that the projection of the object 3 onto the sensor 5 has moved along, in each case, between the individual images by one line pitch d. Thus, accordingly, line Z5 of the image taken under red light at instant t1 is combined with line Z15 of the image taken under green light at instant t2 and with line Z25 of the image taken under blue light at instant t3 to form the color line F1. Each of the lines Z5, Z15, Z25 can be regarded as a color channel for a different color, and the resulting color line F1 contains the color information of an RGB-image. Analogously, line Z5 of instant t2, line Z15 of instant t3 and line 25 of instant t4 are combined with each other to form the color line F2. Likewise, line Z5 of instant t3, line Z15 of instant t4 and line Z25 of instant t5 are combined with each other to form the color line F3. This process is continued until all color lines have been determined which, in each case, represent a linear section of the object 3 transversely to its conveying direction. The color lines are assembled into an overall color picture 11 (here an RGB-image) which is examined with regard to sorting criteria. If the overall color picture 11 meets the sorting criteria, the control signal CTR is generated. It should be emphasized that, according to the process according to the invention, a multicolored image is generated, although all lines which have been read out contain only monochromatic luminance information. However, the color information is reconstructable due to the illumination with different colors. Furthermore, it should be mentioned that all the color lines F1, F2, F3 etc. of the overall color picture 11 have a distance of one line pitch d relative to each other. For a higher resolution, it is required to read out more lines from each image and/or to reduce the time intervals between the individual light pulses.

Figure 5:
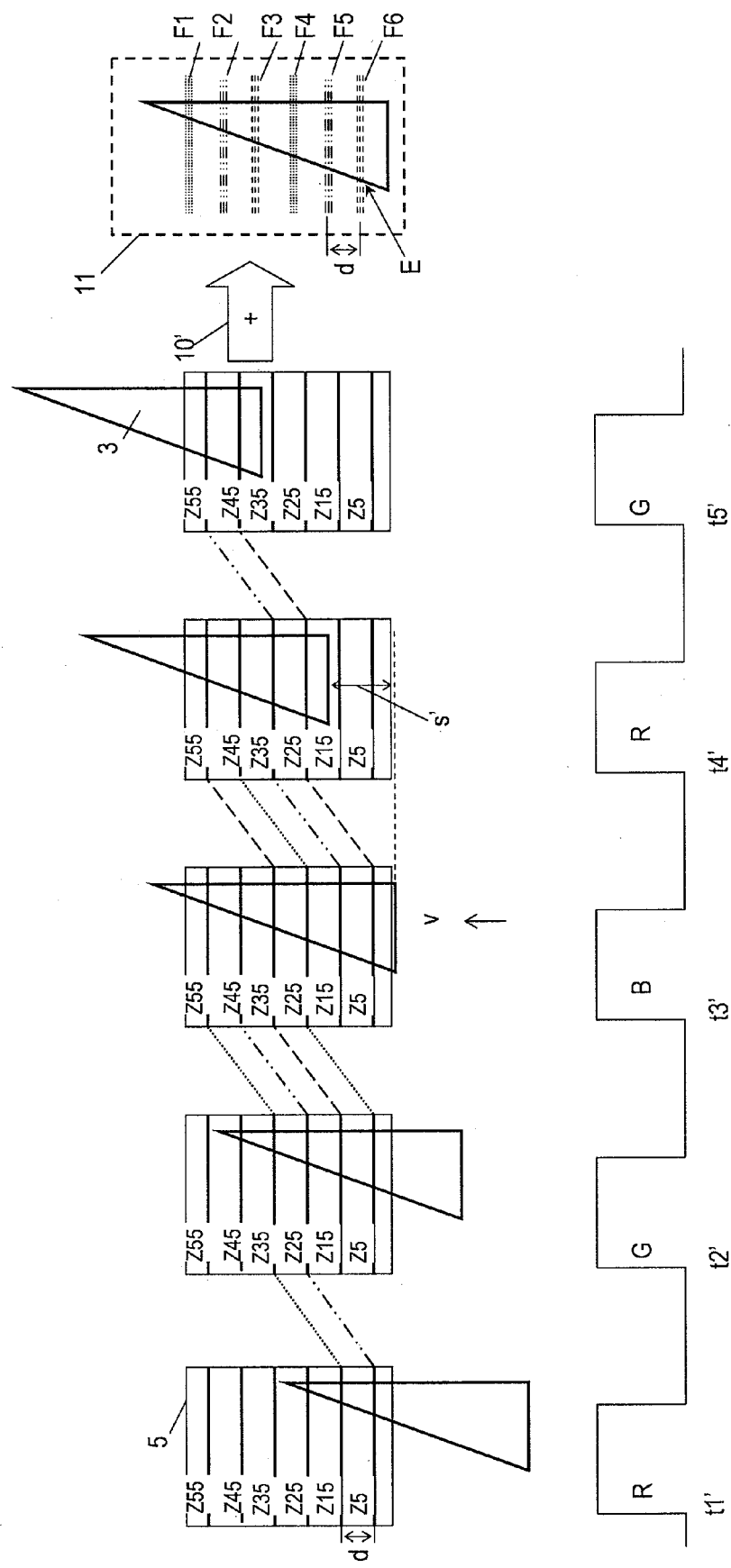
FIG. 5 shows a third path-time characteristic of a temporal sequence of light pulses and image recordings by an optical area sensor and the corresponding route of the object in the conveying direction.

With reference to FIG. 5, it is now shown how, by means of the process according to the invention, significant advantages can be achieved by reading out a larger number of sensor lines than there are different light colors which are being used. In one use case, a multiple of the object resolution can be achieved with an unchanged recording frequency. A further use case allows to get by with a fraction of the recording frequency at an unchanged object resolution and, hence, to achieve a multiplication of the light pulse intervals and thus of the light energy/exposure. The illustration of FIG. 5 corresponds to that of FIG. 2, except for the difference that the time sequence t1'-t5' constitutes twice the time span of the time sequence illustrated in the sequence t1-t5 of FIG. 2. This is also noticeable from the fact that the distance s' for which the object 3 moves along at the conveying speed v between consecutive light pulses has twice the length of the distance s in FIG. 2, as is illustrated by means of the following formulae:

$$t2'-t1'=2\times(t2-t1)$$

$$s'=2\times s$$

Furthermore, per image taken, twice as many lines as there are different colors for the illumination are read out, i.e., six lines. These are lines Z5, Z15, Z25, Z35, Z45, Z55, which, in each case, have a line pitch d of 10 lines, which has been determined as described above. The simplifying assumption applies that the detector exhibits merely 60 lines. The recording situation, which is different from FIG. 2, has to be taken into account by an adapted addition algorithm 10'. As a result of the fact that, per light color, twice as many sensor lines as in the first example are recorded, the addition algorithm 10' also provides twice as many color lines as in the above example for the same number of pulses of light. By the addition algorithm 10', line Z15 of the image taken under red light at instant t1' is now combined with line Z35 of the image taken under green light at instant t2' and with line Z55 of the image taken under blue light at instant t3' to form the color line F1. Analogously, the lines Z5 of t1', Z25 of t2' and Z45 of t3' are combined to form F2,
Z15 of t2', Z35 of t3' and Z55 of t4' are combined to form F3,
Z5 of t2', Z25 of t3' and Z45 of t4' are combined to form F4,
Z15 of t3', Z35 of t4' and Z55 of t5' are combined to form F5, and
Z5 of t3', Z25 of t4' and Z45 of t5' are combined to form F6.

The color lines F1, F2, F3, F4, F5, F6 etc. are assembled into an overall color picture 11.

Figure 3:
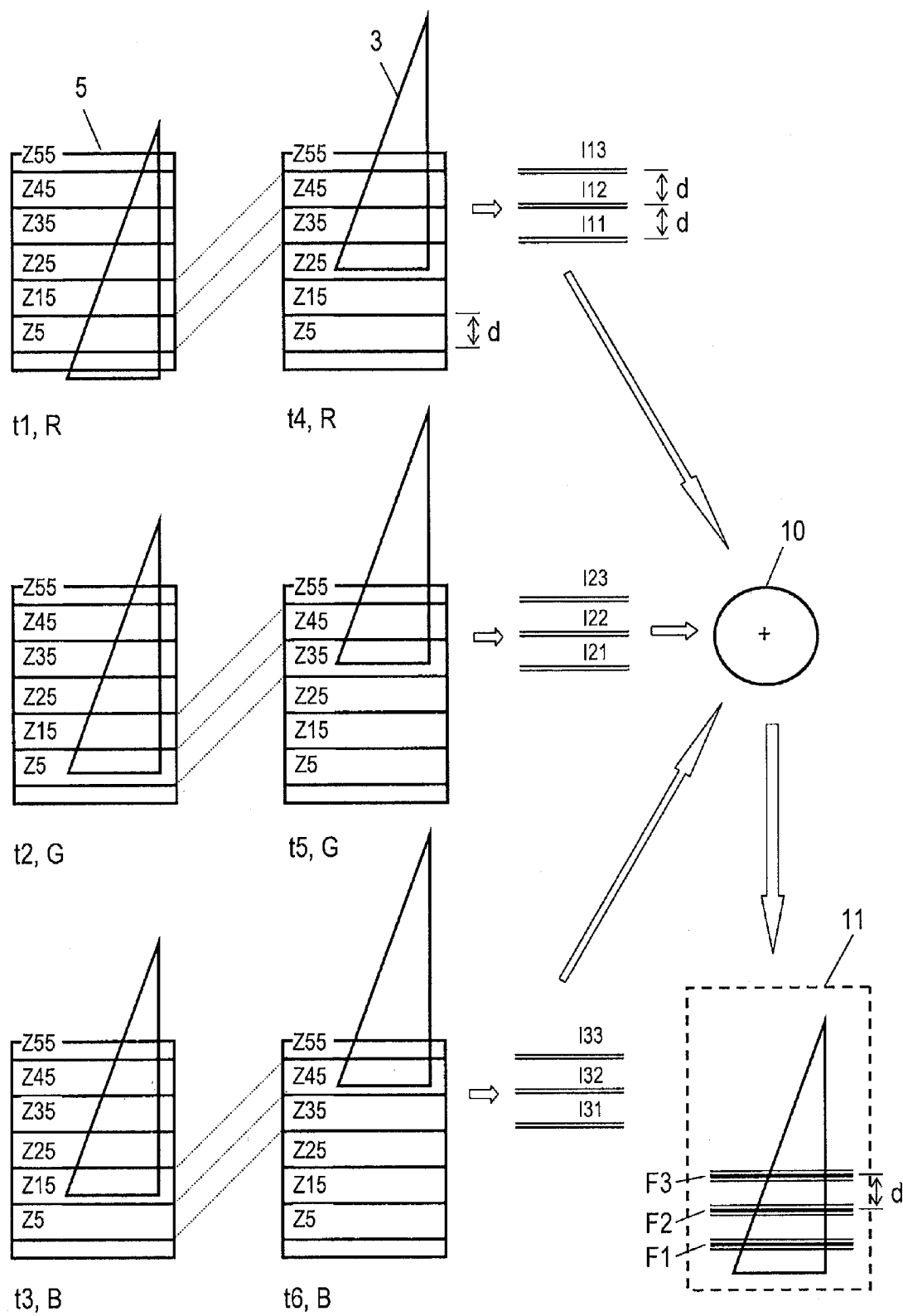
FIG. 3 shows a second path-time characteristic of a temporal sequence of light pulses and image recordings by an optical area sensor and the corresponding route of the object in the conveying direction.

On the basis of the diagrams and illustrations of FIG. 3, it is now shown how, by means of the process according to the invention, the luminous intensity necessary for illuminating the object 3 can be reduced down to a fraction. The illustration of FIG. 3 corresponds to that of FIG. 2, except for the difference that two sequences (t1-t3; t4-t6) of light pulses are illustrated in different colors R, G, B and that, per image taken, twice as many lines as there are different colors for the illumination are read out, i.e., six lines. These are lines Z5, Z15, Z25, Z35, Z45, Z55, which, in each case, have a line pitch d of 10 lines, which has been determined as described above. In contrast to the process described above on the basis of FIG. 2, in the variant of the invention according to FIG. 3, those lines of the two light pulse sequences which have been recorded under illumination with light of the same color are initially added to each other in consideration of the fact that the projection of the object 3 moves along from sequence to sequence. For reasons of minimizing the computational effort in the computer 6, the break between the individual sequences has been determined to have the same duration as the time interval between the individual light pulses within one sequence. The line pitch between two sequences is thus 30 lines. This means that the following line additions are performed:

line Z5 of instant t1 and line Z35 of instant t4 to interline I11;
line Z15 of instant t1 and line Z45 of instant t4 to interline I12;
line Z25 of instant t1 and line Z55 of instant t4 to interline I13;
line Z5 of instant t2 and line Z35 of instant t5 to interline I21;
line Z15 of instant t2 and line Z45 of instant t5 to interline I22;
line Z25 of instant t2 and line Z55 of instant t5 to interline I23;
line Z5 of instant t3 and line Z35 of instant t6 to interline I31;
line Z15 of instant t3 and line Z45 of instant t6 to interline I32;
line Z25 of instant t3 and line Z55 of instant t6 to interline I33.

The interlines I11, I12, I13 contain only luminance information of images taken under red illumination.

The interlines I21, I22, I23 contain only luminance information of images taken under green illumination.

The interlines I31, I32, I33 contain only luminance information of images taken under blue illumination.

In the following, the interlines of different colors are assembled into color lines F1, F2, F3 etc. according to the addition algorithm 10 (analogously to FIG. 2), in consideration of the line pitch d. For example, the color line F1 is assembled from interlines I11, I22, I33. For the color lines F2 and F3, interlines I12 and I13 are used as a red channel, however, for the green channel and the blue channel, interlines which have been detected earlier or future interlines, which, for the sake of clarity, are not illustrated in FIG. 3, would have to be accessed. However, the principle of the assembly becomes comprehensible for everyone from FIG. 3. The color lines F1, F2, F3 etc. are assembled into an overall color picture 11.

Figure 4:
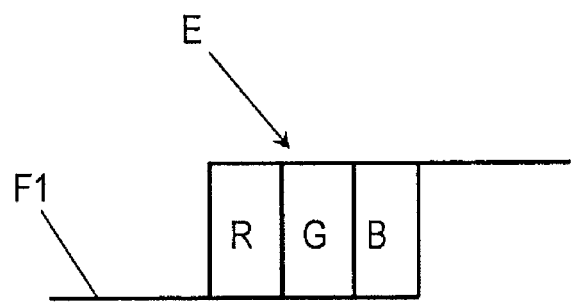
FIG. 4 shows the typical color distribution on the edges of objects during the sequential determination according to the invention of an overall picture of an object.

Below, it is explained on the basis of FIG. 2 and FIG. 4 how, according to the invention, the conveying speed of the object 3 can be determined from the signals of the combined color lines. Namely, it is characteristic of the color lines that, in the illustration of object 3, a clear sequence of the illumination colors R, G, B is visible on the edges thereof, as is illustrated in FIG. 4 for dot E of color line F1. In combination, however, the sequence of the illumination colors R, G, B produces a grey scale value without a resulting color portion. However, in case a resulting color portion arises, this indicates that the temporal sequence of light pulses and the line pitch d of the read-out lines, respectively, do not correspond precisely to the conveying speed v of the object 3. Furthermore, it is possible to discern from the resulting color whether the conveying speed v is too low or too high and also by how much the conveying speed v deviates from the desired value, which is precisely known from the preadjustment of the sequence of light pulses and of the line pitch d. Thus, a speed measurement of the object 3 can be conducted, which is very important for sorting systems, since it is possible, for example, to calculate therefrom precisely when the object 3 will reach the sorting device 9. Furthermore, the measurement according to the invention of the actual conveying speed from the color distributions on the object's edges can be used for readjusting the drive speed of the drive roll 8 and hence for readjusting the conveying speed v of the object 3. A further application of the measurement according to the invention of the actual conveying speed of the objects consists in readjusting the preset line pitch d of the read-out lines until a resulting color portion is no longer visible in the overall color picture G of the object 3 on the object's edges. Complex calibration and recalibration operations can be omitted due to this self-adjusting system 1.

What is claimed is:

1. A process for the optical detection of objects moved at a conveying speed (v), characterized by:
    illuminating the object in a temporally consecutive manner with a sequence of at least two light pulses which exhibit different colors;
    taking images of the object during each light pulse with a monochromatic optical area sensor, comprising a plurality of sensor lines;
    reading out and temporarily storing at least as many lines (Z5, Z15 . . . Z55) of each image as there are different colors of the light pulses, wherein the read-out lines have a line pitch (d) relative to each other by which or by a multiple of which line pitch the projection (P) of the object onto the area sensor moves along between consecutive light pulses (R, G, B) and the line pitch (d) or a multiple thereof, respectively, is proportional to the distance (s, s') for which the object moves along at the conveying speed (v) between consecutive light pulses;
    sequentially combining lines (Z5, Z15 . . . Z55) from images taken under illumination in different colors to form color lines (F1-F6), with the lines (Z5, Z15 . . . Z55) combined with each other having the aforesaid line pitch (d) or a multiple thereof, respectively, relative to each other when they are being read out; and
    assembling the color lines (F1-F6) into an overall color picture.

2. A process according to claim 1, characterized in that the sequence of light pulses is adjusted such that the projection (P) of the object between two light pulses moves along by one line pitch (d) between the lines (Z5, Z15 . . . Z55) to be read out, wherein lines (Z5, Z15 . . . Z55) from the images taken under a consecutive illumination in different colors are combined sequentially to form the color lines (F1, F2, F3), with the lines (Z5, Z15 . . . Z55) combined in this way having the aforesaid line pitch (d) relative to each other when they are being read out.

3. A process according to claim 1, characterized by reading out and temporarily storing a multiple of, at least twice as many lines (Z5, Z15 . . . Z55) of each image as there are different colors of the light pulses (R, G, B), and sequentially combining those monochromatic lines (Z5, Z15 . . . Z55) which have been recorded under illumination with the same color in different sequences of the light pulses (R, G, B) to form interlines (I11, I12, I13; I21, I22, I23; I31, I32, I33), in consideration of the distance between the light sequences and of the line pitch (d) within the sequences, as well as subsequently combining the interlines (I11, I12, I13; I21, I22, I23; I31, I32, I33) allocated to different illumination colors to form color lines (F1, F2, F3), in consideration of the line pitch (d), and assembling the color lines (F1, F2, F3) into an overall color picture.

4. A process according to claim 1, characterized in that the sequence of the light pulses is adjusted such that the projection (P) of the object between two light pulses moves along by an integral multiple of, at least twice, the line pitch (d) between the lines (Z5, Z15 . . . Z55) to be read out, wherein lines (Z5, Z15 . . . Z55) from the images taken under illumination in different colors are combined sequentially to form the color lines (F1-F6), with the lines (Z5, Z15 . . . Z55) combined with each other having the aforesaid multiple of the line pitch (d) relative to each other when they are being read out.

5. A process according to claim 1, characterized in that fast-switching, narrowband to monochromatic light sources (LQ1, LQ2, LQ3, LQ4), preferably light emitting diodes or lasers, are used for the illumination.

6. A process according to claim 1, characterized in that the object is moved on a transparent transport device and the illumination of the object occurs through the transport device, with the optical area sensor being positioned on the same side of the transport device as is the object.

7. A process according to claim 1, characterized in that the light sources (LQ3, LQ4) for the illumination of the object and the optical area sensor are positioned on the same side of the transport device as is the object.

8. A process according to claim 1, characterized in that sequences of the illumination colors of the light pulses (R, G, B) on edges (E) of the object are determined from color lines (F1, F2, F3) and the sequence of the illumination colors is combined and it is determined whether the combination signal constitutes a pure luminance value without a color portion or exhibits a resulting color portion, wherein the color of a resulting color portion, which optionally exists, is a measure of the deviation of the actual speed of the object from the desired conveying speed (v) and the actual speed of the object is calculated therefrom.

9. A process according to claim 8, characterized in that the drive speed of the driving device of the transport device is readjusted upon detecting a deviation of the actual speed of the object from the desired conveying speed (v).

10. A process according to claim 8, characterized in that the line pitch (d) is readjusted upon detecting a deviation of the actual speed of the object from the desired conveying speed (v).

11. A process according to claim 1, wherein the optical area sensor comprises a CMOS sensor.

\* \* \* \* \*